US00PP36623P2

(12) United States Plant Patent
van Swieten

(10) Patent No.: US PP36,623 P2
(45) Date of Patent: Apr. 22, 2025

(54) ***PHALAENOPSIS* PLANT NAMED 'PHA906965'**

(50) Latin Name: *Phalaenopsis hybrida*
Varietal Denomination: PHA906965

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/586,510

(22) Filed: Feb. 25, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

PUBLICATIONS

UPOV Pluto 20240916 retrieved on Sep. 19, 2024 at https://pluto.upov.int/result, one page. (Year: 2024).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA906965', characterized by its relatively compact and upright plant habit; moderately vigorous growth habit and moderate growth rate; strong flowering stems; strong leaves; freely flowering habit with typically two inflorescences developing per plant, each inflorescence with numerous flowers; white-colored flowers with reddish purple-colored labella; and good postproduction longevity.

2 Drawing Sheets

Figure 1:
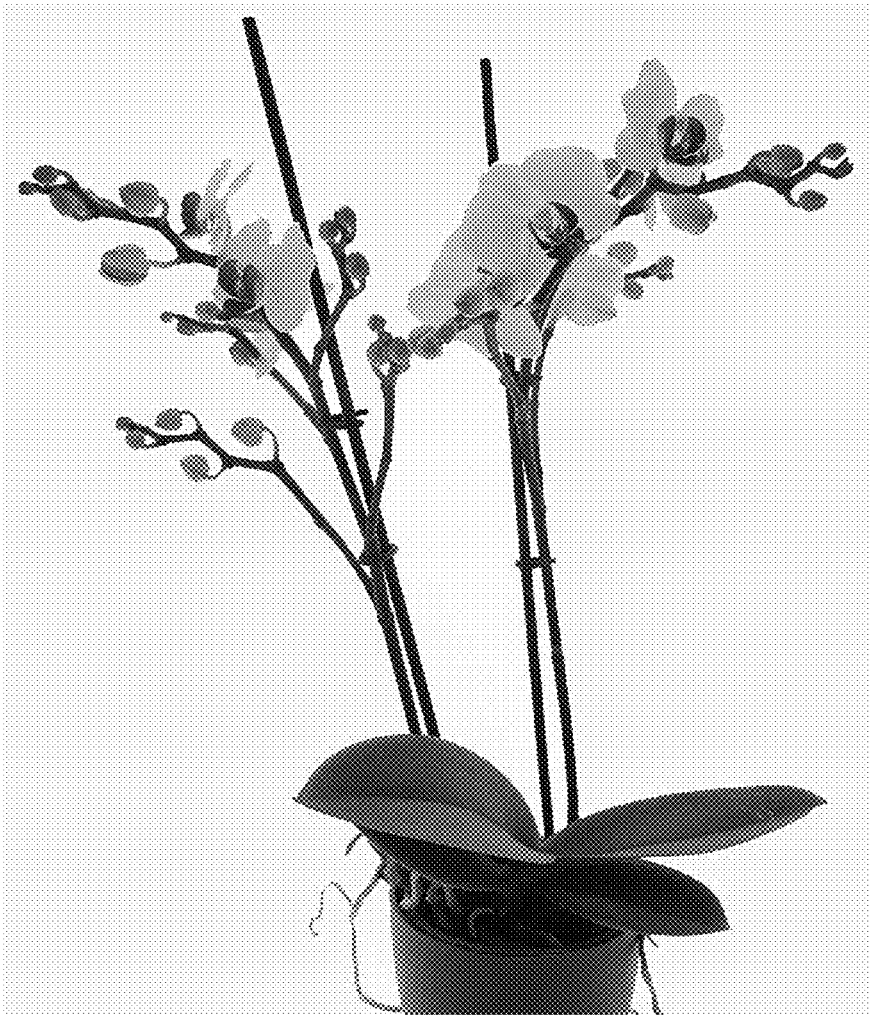

Botanical designation: *Phalaenopsis hybrida.*
Cultivar denomination: 'PHA906965'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B.V. of Bleiswijk, The Netherlands on Aug. 24, 2022, application number 2022/1982. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA906965'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique and attractive patterns and coloration.

The new *Phalaenopsis* plant originated from a cross-pollination in February 2012 in Bleiswijk, The Netherlands of a proprietary selection of *Phalaenopsis hybrida* identified as code number 28703-0001, not patented, as the female, or seed, parent with a proprietary selection of *Phalaenopsis hybrida* identified as code number 20371-0004, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in May 2015.

Asexual reproduction of the new *Phalaenopsis* plant by in vitro meristem propagation in a controlled environment in Bleiswijk, The Netherlands since May 2015 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA906965'. These characteristics in combination distinguish 'PHA906965' as a new and distinct *Phalaenopsis* plant:

1. Relatively compact and upright plant habit.
2. Moderately vigorous growth habit and moderate growth rate.
3. Strong flowering stems.
4. Strong leaves.
5. Freely flowering habit with typically two inflorescences developing per plant, each inflorescence with numerous flowers.
6. White-colored flowers with reddish purple-colored labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are semi-erect whereas leaves of plants of the female parent selection are horizontal.
2. Lateral labellum lobes of plants of the new *Phalaenopsis* are orbicular in shape whereas lateral labellum lobes of plants of the female parent selection are semi-circular in shape.

Plants of the new *Phalaenopsis* can be compared to plants of the male parent selection. Plants of the new *Phalaenopsis* differ primarily from plants of the male parent selection in the following characteristics:

1. Flower petals and sepals of plants of the new *Phalaenopsis* are white in color whereas flower petals and sepals of plants of the male parent selection are purplish pink in color.
2. Apical lobes of the labellum of plants of the new *Phalaenopsis* are reddish purple color whereas apical lobes of the labellum of plants of the male parent selection are yellow in color.
3. Lateral labellum lobes of plants of the new *Phalaenopsis* are orbicular in shape whereas lateral labellum lobes of plants of the male parent selection are semi-circular in shape.

Plants of the new *Phalaenopsis* can be compared to plants of *Phalaenopsis hybrida* 'Phalfytyo', disclosed in U.S. Plant Pat. No. 30,609. In side-by-side comparisons, plants of the new *Phalaenopsis* differ primarily from plants of 'Phalfytyo' in the following characteristics:

1. Flower petals of plants of the new *Phalaenopsis* are almost twice as broad as flower petals of plants of 'Phalfytyo'.
2. Flower petals and sepals of plants of the new *Phalaenopsis* are white in color whereas flower petals and sepals of plants of 'Phalfytyo' are white in color with slightly red purple-colored centers.
3. Lateral labellum lobes of plants of the new *Phalaenopsis* are more curved than lateral labellum lobes of plants of 'Phalfytyo'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA906965' grown in a container.

Figure 2:
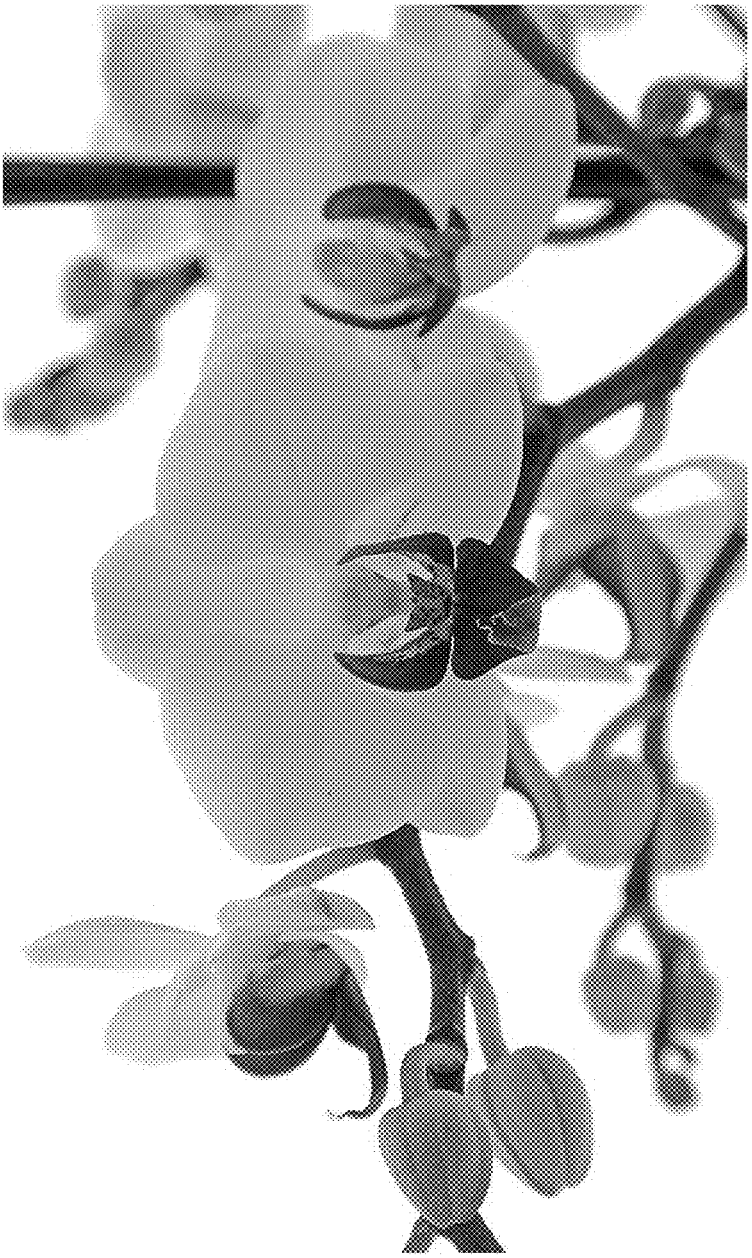

The photograph on the second sheet (FIG. 2) is a close-up view of typical flowers of 'PHA906965'.

DETAILED BOTANICAL DESCRIPTION

The aforementioned photographs and following observations and measurements describe plants grown during the autumn in 9-cm containers in a glass-covered greenhouse in Bleiswijk, The Netherlands and under cultural practices typically used in commercial *Phalaenopsis* production. Plants were 16 months old when the photographs and description were taken. During the first 13 months of production of the plants, day and night temperatures averaged 28.5° C.; and during the last three months of production of the plants, day and night temperatures averaged 20° C. In the following description, color references are made to The Royal Horticultural Society Colour Chart, 2015 Edition, except where general terms of ordinary dictionary significance are used.

Botanical classification: *Phalaenopsis hybrida* 'PHA906965'.

Parentage:

*Female, or seed, parent*.—Proprietary selection of *Phalaenopsis hybrida* identified as code number 28703-0001, not patented.

*Male, or pollen, parent*.—Proprietary selection of *Phalaenopsis hybrida* identified as code number 20371-0004, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; dense.

Plant description:

*Plant form and growth habit*.—Herbaceous epiphyte; relatively compact and upright plant habit with typically two inflorescences developing per plant, each inflorescence with numerous flowers; monopodial; moderately vigorous growth habit and moderate growth rate.

*Plant height, substrate level to top of foliar plane*.—About 5.8 cm.

*Plant height, substrate level to top of floral plane*.—About 30.7 cm.

*Plant diameter or spread*.—About 22.8 cm.

Leaf description:

*Arrangement and quantity*.—Distichous, simple; sessile; about four fully-developed leaves per plant.

*Length*.—About 10.9 cm.

*Width*.—About 5 cm.

*Aspect*.—Semi-erect; flat to slightly curled downwardly.

*Shape*.—Ovate to elliptic-oblong; slightly carinate.

*Apex*.—Unequal and broadly acute.

*Base*.—Sheathing. Sheath length: About 1.4 cm. Sheath width: About 1 cm. Sheath color: Close to a blend of 143C and 144A; towards the margins, close to a blend of 143B and 144A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to 146A; narrow marginal edge, close to N200A. Developing leaves, lower surface: Close to 146B; narrow marginal edge, close to a blend of N200A and N200B. Fully expanded leaves, upper surface: Close to a blend of NN137B and 146B; narrow marginal edge, close to N200B; venation, close to NN137A. Fully expanded leaves, lower surface: Close to 146B; narrow marginal edge, close to a blend of N200B and N200C; venation, close to 138A and 138B.

Inflorescence description:

*Appearance and flowering habit*.—Showy zygomorphic flowers arranged on axillary simple or branched racemes; typically two inflorescences develop per plant; each inflorescence with about 22 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 14 weeks on the plant; flowers not persistent.

*Inflorescence length* (*lowermost flower to inflorescence apex*).—About 22 cm.

*Inflorescence width*.—About 15.7 cm.

*Flower buds*.—Height: About 1.4 cm. Diameter: About 1.1 cm by 1.3 cm. Shape: Broadly ovate. Color: Close to a blend of 145D and 150D; towards the base, close to 150D, and tinged towards the apex with close to 185C.

*Flower size*.—About 5 cm (vertical) by 5.2 cm (horizontal).

*Flower depth*.—About 2.3 cm.

*Petals, quantity and arrangement*.—Three, two "free" (not imbricate), lateral petals and one center petal transformed into a labellum.

*Lateral petals*.—Length: About 2.6 cm. Width: About 3 cm. Shape: Broadly deltoid-reniform. Apex: Broadly and bluntly acute. Margin: Entire; not undulate. Texture and luster, upper and lower surfaces: Smooth, glabrous, moderately velvety; matte. Color: When opening and fully opened, upper surface: Close to NN155D; color does not change with subsequent development. When opening and fully opened, lower surface: Close to NN155D; towards the center, very slightly tinged with close to 76A; color does not change with subsequent development.

*Labella*.—Appearance: Three-parted with two lateral lobes and a separate, non-fused central lobe. Length, lateral lobes: About 1.5 cm. Width, lateral lobes: About 1 cm. Length, central lobe: About 1.4 cm. Width, central lobe: About 5 mm to 14 mm. Length, cirrhose tips: About 5 mm. Shape, lateral lobes: Obovate, slightly curved inwardly. Shape, central lobe: Deltoid with a slightly elongated apex. Apex, lateral lobes: Obtuse. Apex, central lobe: Cleft with two upwardly reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 5 mm in width and about 4 mm in height. Color: When opening and fully opened, upper surface: Lateral lobes: Close to 72B; margins, close to a blend of 59A and 187B; towards the base, close to 11C with axial stripes and sparse dots, close to a blend of 59A and 187B. Central lobe: Close to a blend of 59A and 187B; toward the apex, close to 71A and 72A; at the base, close to N155A; near the callosities, marbled with a blend of 59A and 187B; cirrhose tips, close to 11A. Callosities: Close to 12A; outer sides, close to 10D; at the apex, finely dotted with close to 59A. When opening and fully opened, lower surface: Lateral lobes: Close to 72B; towards the margins, close to 183A; at the base, close to 156C and 156D. Central lobe: Close to N155A; towards the column, close to 157A; broad part strongly tinged with close to 11A; margins, close to a blend of 59A and 187B and distally, close to 72B and 77B; cirrhose tips, close to 11A and proximally, close to N155A.

*Sepals*.—Quantity and arrangement: Three, one upper dorsal sepal and two lower lateral sepals. Length, dorsal sepal: About 2.6 cm. Width, dorsal sepal: About 2.1 cm. Length, lateral sepals: About 2.8 cm. Width, lateral sepals: About 1.7 cm. Shape, dorsal sepal: Broadly elliptic. Shape, lateral sepals: Ovate to elliptic. Apex, dorsal sepal: Retuse. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to NN155D; towards the apex, very slightly tinged with close to 76C. When opening, lower surface: Close to NN155A and NN155B; towards the apex, strongly tinged with close to N75B. Fully opened, upper surface: Close to NN155D; towards the apex, very slightly tinged with close to 76C. Fully opened, lower surface: Close to NN155D; towards the apex, tinged with close to N75D. Color, lateral sepals: When opening, upper surface: Close to NN155D; towards the base, close to 157A and 157B; main vein, slightly tinged with close to 71A. When opening, lower surface: Close to NN155C; towards the base, close to 157A and 157B; main vein, strongly tinged with close to 72B. Fully opened, upper surface: Close to NN155C and NN155D; main vein and base, slightly tinged with close to 71A; color does not change with subsequent development. Fully opened, lower surface: Close to NN155C and NN155D; main vein, strongly tinged with close to 72B; color does not change with subsequent development.

*Peduncles*.—Length: About 33.1 cm. Diameter: About 4 mm. Strength: Strong. Aspect: Upright to outwardly arching. Texture and luster: Smooth, glabrous; matte. Color: Close to 200A and 200B; heavily dotted with fine dots, darker than 146C.

*Pedicels*.—Length: About 2.3 cm. Diameter: About 3 mm. Strength: Moderately strong. Aspect: About 80 degrees from peduncle axis. Texture and luster: Smooth, glabrous; matte. Color: Close to 155B and 155C; distally, tinged with close to 75C, and fading to close to N148A.

*Reproductive organs*.—Androecium: Column length: About 8 mm. Column width: About 5 mm. Column color: Close to NN155D; distally on lower surface, close to N78B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to N155A. Ovary length: About 5 mm. Ovary diameter: About 1 mm. Ovary color: Close to 149C and 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA906965' as herein illustrated and described.

* * * * *